United States Patent
Greco et al.

(10) Patent No.: US 7,989,502 B2
(45) Date of Patent: Aug. 2, 2011

(54) INTRANASAL DELIVERY OF MODAFINIL

(75) Inventors: Mary Ann Katherine Greco, San Francisco, CA (US); William Howard Frey, II, White Bear Lake, MN (US); Jacqueline DeRose, Santa Clara, CA (US); Rachel Beth Matthews, Dayton, MN (US); Leah Ranae Bresin Hanson, Vadnais Heights, MN (US)

(73) Assignees: SRI International, Menlo Park, CA (US); HealthPartners Research Foundation, Minneapolis, MN (US)

( * ) Notice: Subject to any disclaimer, the term of this patent is extended or adjusted under 35 U.S.C. 154(b) by 90 days.

(21) Appl. No.: 12/367,496

(22) Filed: Feb. 6, 2009

(65) Prior Publication Data

US 2010/0204334 A1 Aug. 12, 2010

(51) Int. Cl.
*A61K 31/10* (2006.01)
*A61K 31/04* (2006.01)

(52) U.S. Cl. ....................... 514/710; 514/740

(58) Field of Classification Search .................. 514/710, 514/740
See application file for complete search history.

(56) References Cited

U.S. PATENT DOCUMENTS

2003/0171439 A1* 9/2003 Lawyer et al. ................ 514/618
2010/0074959 A1* 3/2010 Hansom et al. ............... 424/489

OTHER PUBLICATIONS

Reger et al. "Intranasal insulin improves cognition and modulates B-amyloid in early AD" Neurology 2008; 70: 440-448.*

* cited by examiner

*Primary Examiner* — Sreeni Padmanabhan
*Assistant Examiner* — Renee Claytor
(74) *Attorney, Agent, or Firm* — Richard Aron Osman

(57) ABSTRACT

Modafinil is selectively delivered to the brain, minimizing delivery to the blood, of a person in need thereof by administering to the person a therapeutically-effective dosage of modafinil, wherein the dosage is less than 1 mg, formulated in a lipid microemulsion (LME) and selectively delivered to the upper third of the nasal cavity. The method may be implemented with an intranasal pharmaceutical delivery device loaded with a modafinil composition and adapted to deliver the dosage to the upper third of the nasal cavity.

21 Claims, No Drawings

INTRANASAL DELIVERY OF MODAFINIL

FIELD OF THE INVENTION

The field of the invention is intranasal delivery of modafinil.

BACKGROUND OF THE INVENTION

Modafinil (sold by Cephalon under the tradename PROVIGIL) is a drug that is used to promote wakefulness, alertness and/or cognitive acuity. Side effects to systemic administration include upset stomach, diarrhea, chest pain, allergic reactions, headache, nervousness, dizziness and anxiety. Modafinil has been subject to a variety of formulations, e.g. U.S. Pat. No. 6,489,363, and intranasal delivery of modafinil has been proposed, e.g. Lawyer, et al. US 2003/0171439; however such conventional intranasal delivery provides unsatisfactory efficacy, requires undesirably large dosages, and yields poor brainiblood delivery ratios.

Inventor Frey has coauthored related issued, published and pending patent applications, including WO/2008/049588 related to intranasal delivery of poorly-water soluble compounds to the brain using lipid formulations, and U.S. Pat. Nos. 5,624,898; 6,180,603; 6,313,093; 6,342,478; 6,407,061; 6,991,785; 7,084,126; PCT publications WO91/07947; WO 00/33813; WO00/33814; WO01/41782; WO02/32449; WO02/086105; WO03/072056; and U.S. patent application/Pub Ser. Nos. 09/458,566; 09/458,562; 20030072793; 20020072498; 20020082215; 20020169102; 60/285,319; 60/288,716; 60/601,547; 2006/0188496; 2007/0092500; 2007/0054843; 20070093420.

SUMMARY OF THE INVENTION

The invention provides methods, compositions and devices for delivering modafinil selectively to the brain, minimizing delivery to the blood, of a person in need thereof. The invention may be used to increase wakefulness, attention, alertness and/or cognitive function; reduce sleepiness, drowsiness, tiredness, lethargy, somnolence or symptoms of narcolepsy, and assist personnel such as machine operators and military personnel including pilots to stay awake and alert.

In one embodiment, the invention provides a method for delivering modafinil to a person in need thereof, comprising: administering to the person a therapeutically-effective dosage of modafinil, wherein the dosage is less than 1 mg, formulated in a lipid microemulsion (LME) and selectively delivered to the upper third of the nasal cavity.

The invention encompasses all alternative combinations of more particularly described embodiments:

wherein the dosage is at least 1, 2, 5, 10, 20 or 50 ug and less than 500, 200, 100, 50, 20 or 10 ug, preferably about 10-50, 20-40, or 30 ug.

wherein the dosage is formulated in the LME by adding the modafinil to the LME titrated to pH 7-9, preferably pH 8.

wherein the dosage is formulated in the LME by adding the modafinil to the LME titrated to pH 7-9, preferably pH 8, and then sonicating to dissolve or stably incorporate the modafinil in the LME to form homogeneous modafinil-LME.

wherein the dosage is formulated in the LME by adding the modafinil to the LME titrated to pH 7-9, preferably pH 8, and then sonicating to dissolve or stably incorporate the modafinil in the LME to form homogeneous modafinil-LME, and then titrating the homogeneous modafinil-LME to 7.4.

wherein the dosage is formulated in the LME by adding the modafinil to the LME titrated to pH 7-9, preferably pH 8, and then sonicating.

wherein the dosage is formulated in the LME by adding the modafinil directly to the LME without the use of a cosolvent, such as DMSO.

wherein the dosage is formulated in the LME by adding the modafinil dissolved in a cosolvent, such as DMSO or ethanol to the LME, particularly wherein the final DMSO concentration is less than 5, 2, 1, 0.5, 0.2 or 0.1%.

wherein the dosage is formulated in the LME at a concentration of 0.02, 0.05 or 0.1 to 0.2, 0.5, 1 or 2 mg/ml, preferably 0.02, 0.05, 0.1, 0.2, 0.5, 1 or 2 mg/ml.

wherein the dosage is administered in a volume of 10, 20, 50 or 100 ul to 200, 250 or 400 ul, preferably 10, 20, 50, 100, 200, 250 or 400 ul.

wherein the LME is made of olive oil and phosphatidylserine, preferably in equal amounts, sonicated in a buffer, such as succinate at pH 4.25 or phosphate buffer, at pH 6-9 or 7-8, preferably pH 6, 7 or 8. The pH may then be titrated to optimize addition of the modafinil, such as raising the pH to 7.4.

wherein the modafinil is the R-enantiomer (Armodafinil).

whereby at least 0.02, 0.05, 0.1, 0.5, 1, 2, 5 or 10% of the dosage is delivered to the brain.

whereby less than 50, 20, 10 or 5% of the dosage is delivered to the blood.

wherein the method further comprises the antecedent step of formulating the modafinil in the LME, and optionally, between the formulating and administering steps the modafinil is protected from light and maintained at 2, 4, 10 or 15° C. to 15, 20 or 30° C., or at room temperature.

wherein the method further comprises the subsequent step of detecting a resultant therapeutic effect; such as increased wakefulness, attention, alertness and/or cognitive function; reduced sleep, sleepiness, drowsiness, tiredness, lethargy, somnolence, or symptoms of narcolepsy.

wherein the method further comprises the subsequent step of detecting or quantifying a resultant delivery of the modafinil to the brain or blood, such as by MRI, PET imaging, HPLC, immunoassay (ELISA), etc.

wherein the dosage is selectively delivered to the upper third of the nasal cavity by snorting.

wherein the dosage is selectively delivered to the upper third of the nasal cavity using a VIANASE electronic atomizer or an OPTINOSE nasal delivery system.

In another embodiment the invention provides a pharmaceutical composition adapted for practicing the subject methods including specific embodiments thereof, and generally consisting essentially of a therapeutically-effective, unit dosage of modafinil, wherein the dosage is less than 1 mg, formulated in a lipid microemulsion (LME).

In another embodiment the invention provide intranasal pharmaceutical delivery devices adapted for practicing the subject methods and loaded with a subject pharmaceutical composition and adapted to deliver the dosage to the upper third of the nasal cavity.

DETAILED DESCRIPTION OF SPECIFIC EMBODIMENTS OF THE INVENTION

We have developed novel methods and compositions for selectively targeting modafinil to the brain while minimizing delivery to the blood. Our intranasal delivery methods can bypass the blood-brain barrier, to target modafinil directly to the brain from the nasal mucosa. Using our methods modafinil does not have to enter the blood to reach the brain, so deep intranasal treatment minimizes or avoids not only metabolism and elimination by the liver and kidneys and binding by plasma proteins, but also unwanted systemic exposure and side-effects. Using our methods, direct delivery from the nasal mucosa to the brain occurs rapidly, within minutes in animals and humans, allowing for rapid onset of action. A lower dose can therefore be administered.

Our solution provides numerous advantages over prior methods of administration:

Since modafinil does not have to enter the blood to reach the brain, intranasal treatment avoids not only metabolism and elimination by the liver and kidneys and binding by plasma proteins, but also unwanted systemic exposure and side-effects.

Direct delivery from the nasal mucosa to the brain occurs rapidly, within minutes in animals and humans, allowing for rapid onset of action.

No alteration of modafinil is required.

Lower doses are required than with oral treatment or conventional nasal delivery, and GI side effects are minimized or eliminated.

The nasal spray can be applied quickly using one hand without any need for a glass of water to take a pill which will increase compliance.

Intranasal targeting of modafinil to the brain using our methods provides enhanced efficacy to reduce sleepiness and increase attention and performance.

Our methods and compositions are particularly beneficial for individuals in need of improved alertness, attention and/or memory, such as individuals with narcolepsy, shift work sleep disorder (SWSD), obstructive sleep apnea/hypopnea syndrome (OSA/HS), individuals who need to function on a limited amount of sleep such as defense personnel, pilots or medical personnel, and patients suffering from fatigue, inattention, memory loss, etc. from disease (e.g. patients with Alzheimer's disease and other forms of dementia) or therapy (e.g. chemotherapy).

We have validated several alternative methods for delivering the recited therapeutically-effective dosage to the upper third of the nasal cavity, above the lower turbinates where conventional intranasal delivery deposits drugs. These method selectively, preferentially and/or enrichedly deliver to the target upper third of the nasal cavity, as compared with conventional intranasal delivery, such as intranasal drops and mists, and employ a protocol or device adapted to this delivery. For example, one method is a snort delivery, such as exemplified in our rat studies below. Prior studies using dyes and radiolabeled drug demonstrated preferential delivery to the upper third of the nasal cavity, e.g. Thorne et al., Neurosci 127 (2004) 481-496. With one side (naris) of the nose covered, the rat snorts the drop high into the nasal cavity reaching the roof of the nasal cavity and exposing the olfactory epithelium with its olfactory nerves that travel from the nose to the brain. The drug travels via a rapid extracellular pathway along these nerves into the brain bypassing the blood-brain barrier. We have also shown that drugs administered this way can travel along the trigeminal neural pathway from the nasal mucosa to the brain. Snort delivery to the upper third of the nasal cavity is also effective in humans e.g. Reger, et al., Neurbio Aging 27, 451-8 (2006); Foltin et al., Pharmacol Biochem Behav. 2004 May; 78(1):93-101; however, preferred human delivery uses a specifically-adapted device, such as a fiber optic guided ENT scope or flexible nasopharyngoscope that can spray the formulations directly on the roof of the nasal cavity, or such as a VIANASE electronic atomizer or an OPTINOSE nasal delivery system, see, e.g. Reger et al., February 2008, Neurol 70, 440-8, or a pressurized olfactory delivery system (e.g. POD device, Impel NeuroPharma, Normandy Park, Wash.). Another applicable method for direct delivery upper third of the nasal cavity, suitable for many target mammals, is intranasal intubation; for example, in monkeys, we have so demonstrated direct delivery from the nose to the brain, e.g. Thorne et al., Neurosci 152 (2008) 785-797.

We have also validated several alternative suitable LME formulations, which generally comprise pharmaceutically-acceptable oil and emulsifier components. Preferred oil components are plant-derived oils, such as olive oil, soybean oil, cottonseed oil, safflower oil, corn oil, coconut oil, sesame oil, peanut oil, and the like. Alternative suitable oils include animal or a fish oil such as cod liver oil, and mineral or chemically-synthesized oils such as 2-linoleoyl-1,3-dioctanoyl glycerol. Semisynthetic mono-, di- or triglycerides may also be used and include rac-glyceryl-1-monopalmitic, acyl glyceryl-1-monoolein, 1,2-dipalmitic, 1,3-dipalmitic, trimyristin, tripalmitin, tristearin, triolein, trilaiden and the like. The oil component may include mixtures of one or more suitable oils.

The emulsifier component is preferably a naturally-occurring phospholipid, particularly a glycerophospholipid, such as phosphatidylcholine, phosphatidylserine, and phosphatidylglycerol; other suitable phospholipids including egg yolk and soybean phospholipids. The emulsifier also can be a synthetic phospholipid such as dihexanoyl-L-$\propto$-lecithin. The emulsifier component may be partially or fully hydrogenated, and may include mixtures of one or more suitable emulsifiers.

The oil and emulsifier components are emulsified, generally by sonication or microfluidization, in a pharmaceutically-acceptable aqueous buffer, such as salts (e.g. sodium or potassium salts) of succinic acid, phosphoric acid, boric acid, citric acid, carbonic acid, hydroxide, and the like; tris(hydroxymethyl)aminomethane (TRIS™ buffer), amino acids, and like buffers.

Particularly preferred, exemplified LME formulations include:

(a) olive oil (extra virgin) and phosphatidylserine (50:50 w/w) sonicated in sodium succinate buffer (50 mM); at pH 8 or titrated from pH4.25 to pH 8 prior to modafinil addition.

(b) soybean oil and phosphatidylcholine (50:50 w/w) sonicated in sodium phosphate buffer at pH 7.

(c) sesame oil and phosphatidylglycerol (50:50 w/w) sonicated in sodium borate buffer at pH 4.

(d) cod liver oil and dihexanoyl-L-$\propto$-lecithin (50:50 w/w) sonicated in potassium citrate buffer at pH 7.8.

(e) 2-linoleoyl-1,3-dioctanoyl glycerol and phosphatidylserine (50:50 w/w) sonicated in TRIS buffer at pH 7.6.

(f) rac-glyceryl-1-monopalmitic and hydrogenated egg yolk phospholipids (50:50 w/w) sonicated in succinate buffer at pH 7.6.

(g) olive oil, soybean oil, phosphatidylserine and phosphatidylcholine (25:25:25:25 w/w) sonicated in succinate buffer at pH 7.

Exemplary validation experiments confirm effective Modafinil-LME formulations in our animal models:

(i) modafinil 2 ug (50 ul of 0.04 mg/ml) delivered in LME (b); snort model, rat.

(ii) modafinil 10 ug (50 ul of 0.02 mg/ml) delivered in LME(g); snort model, rat.

(iii) armodafinil 10 ug (50 ul of 0.02 mg/ml) delivered in LME(a); snort model, rat.

(iv) modafinil 8 ug (400 ul of 20 ug/ml) delivered in LME (a); intranasal intubation, cynomolgus monkey.

(v) modafinil 50 ug (400 ul of 0.125 mg/ml) delivered in LME(a); intranasal intubation, cynomolgus monkey.

(vi) modafinil 200 ug (400 ul of 0.5 mg/ml) delivered in LME(a); intranasal intubation, cynomolgus monkey.

(vii) modafinil 2 ug (100 ul of 0.02 mg/ml) delivered in LME(a); ViaNase, human.

(viii) modafinil 20 ug (100 ul of 0.2 mg/ml) delivered in LME(a); ViaNase, human.

(ix) armodafinil 20 ug (200 ul of 0.1 mg/ml) delivered in LME(b); ViaNase, human.

(x) modafinil 2 ug (200 ul of 0.01 mg/ml) delivered in LME(a); OptiNose, human.

(xi) modafinil 10 ug (200 ul of 0.05 mg/ml) delivered in LME(a); OptiNose, human.

(xii) modafinil 50 ug (200 ul of 0.25 mg/ml) delivered in LME(a); OptiNose, human.

(xiii) modafinil 200 ug (400 ul of 0.5 mg/ml) delivered in LME(a); OptiNose, human.

Note that dosage amounts and volumes are expressed as total dosage amount/dosage, generally equally divided in bilateral administrations.

EXAMPLES

1. Deep intranasal delivery of low-dose, LME modafinil formulations to rats alters sleep-wake behavior in a manner consistent with oral and/or intravenous delivery, dramatically reducing the amount of drug needed to stimulate wakefulness.

Formulation of Intranasal Drugs. Modafinil (Sigma) was solubilized using LME comprised of equal amounts of olive oil and phosphatidyl serine sonicated in succinate buffer, pH 8; modafinil concentrations 0.2 and 2 mg/ml. Control rats received either saline alone or lipid emulsion in succinate buffer, pH 8

Animals and surgery. Anesthetized male Sprague Dawley rats (250-350 g) were implanted with sleep recording electrodes to monitor electroencephalographic (EEG) and electromyographic (EMG) activities. A femoral vein catheter was also implanted and dorsally extended subcutaneously to exit at the posterior end of the EEG/EMG implant. The rats were individually housed in a controlled environment (12 h lights on/off; lights on, 8 am) with access to food and water ad libitum. The animals were allowed to recover for approximately 7-10 days following surgery and habituated to the recording chambers. Baseline behavior was continuously recorded for 48 to 60 h prior to experiment initiation and for at least 24 h post drug administration. Rats were sacrificed by pentobarbital administration (200 mg/kg, i.v.) into the femoral catheter without handling the animal, Greco et al., Neuroscience. 1999; 93(4):1369-74; Vazquez et al., J Cell Biochem. 2008 Dec. 15; 105(6):1472-84.

Intranasal drug delivery—snort model. Three hours into the lights on period, each rat was anesthetized with ~3% isoflurane in $O_2$ and placed on its back. The head and neck of the rat remained flat and horizontal throughout the entire procedure to prevent any drug from draining down the back of the throat. Reflexes were monitored periodically and anesthetic level was reduced to ~1.5% isoflurane in $O_2$ for anesthesia maintenance. Each drug was given in 6-7 ul administered with a manual pipette every 2 minutes into alternating nostrils (total volume=50 ul). Two minutes after the last drop was administered, the rat was removed from anesthesia, reconnected to the tethering cable and placed in the recording chamber. The effect of intranasal drug delivery on sleep-wake behavior was monitored for 24 h post-intranasal drug delivery.

Results. Rats awakened within one minute post modafinil administration. Control rats awoke within 3-5 minutes after termination of anesthesia. EEG and EMG activity during wakefulness, slow wave sleep (SWS), and rapid eye movement (REM) sleep were captured digitally, and subsequently scored manually in 10 sec epochs, averaged into one minute bins and represented graphically by hour for approximately 5 to 8 h post drug delivery. Representative individual hypnograms show the wake-promoting effects via intranasal delivery directly to the CNS. Modafinil induced wakefulness in rats at a 100-fold lower dose via our intranasal route than what has been previously published using traditional routes of administration (ie. i.v., oral). When we attempted to deliver a dose comparable to that given orally, the excitatory effects overcame the anesthesia and the animals woke up.

2. Drug concentrations for effective intranasal delivery.

We designed protocols to further optimize concentrations of sleep and wake promoting drugs for intranasal delivery. In exemplary experiments, the drugs are administered to rats in the following concentrations: Modafinil: 0.2 mg/ml (n=3), 0.1 mg/ml (n=3), 0 (LME only, n=3), and the rats instrumented and tested as detailed above.

In one series of experiments we found an effective concentration of modafinil was 0.05 mg/ml in the lipid microemulsion. The 2.5 ug dose was administered in 50 ul of LME to a 350 g rat. This is equivalent to 0.00714 mg/kg, and based on a human weighing 70 kg, this translates to a human dose of 0.5 mg.

Currently oral modafinil is prescribed in 100 or 200 mg tablets. In our methods effective dosages include 0.25% to 0.50% of the oral dose, and dosages ranging from ~0.01 to ~1.75 mg are effective in humans using our LME formulation and delivery to the upper third of the nasal cavity.

Sleep Scoring and Statistical Analyses. EEG/EMG recordings are scored using SleepSign™ for Animals (Kissei Comtec, Irvine, Calif.), manually verified for accuracy and stored to disk. Waking is identified by the presence of desynchronized EEG readings and high EMG activity. SWS is identified by high amplitude slow waves together with a low EMG tone relative to waking. REM sleep is identified by the presence of regular theta activity coupled with low EMG relative to SWS. REM sleep is scored only when it follows at least a 15 s episode of SWS. All sleep-wake parameters are analyzed for each hour of the recording periods, then averaged to yield 24 h baseline estimates. A similar analysis is performed prior to and post intranasal drug administration. Dependent measures of sleep and wakefulness include: percent total sleep time (TST), percent wake, percent SWS, and percent REM sleep; number of wake, SWS, and REM sleep bouts; and duration of wake, SWS, and REM sleep bouts. The filter settings are the same for all animals; signal amplitude is standardized using a 12-13 Hz signal. Descriptive statistics, ANOVA, and multiple pair-wise comparisons of each experimental condition are used to evaluate changes in the sleep-wake dependent variables listed above. Statistical significance is evaluated at the $p<0.05$ level.

3. Effectiveness under simulated operational conditions.

In our chronic sleep deprivation paradigm rats are deprived of sleep for 6 h on 3 consecutive days starting at the beginning of the lights on period, when the pressure to sleep is maximal. The sleep deprivation begins with the administration of modafinil and is immediately followed by roto-rod testing. EEG/EMG recordings resumes once the rats are returned to the cage. If needed, the rats are kept awake for the remainder of the deprivation period by gentle handling. At the end of the sleep deprivation, the rats are again subjected to roto-rod testing. The sleep deprivation protocol is executed for 3 consecutive days. On the third day, half of the rats are sacrificed immediately following the sleep deprivation period. A second group of rats are sacrificed after 1-2 h of recovery sleep (RS). The sleep deprivation takes place after recovery from surgery (Pre-Week 1) and training on the roto-rod (Pre-Week 2).

In this protocol, the intranasal delivery of modafinil is assayed by two behavioral indicies—EEG/EMG recordings of sleep-wakefulness and performance (wheel running, roto-rod assay). A total of 12 rats are tested under these conditions. Due to the timing of the sleep deprivation and the roto-rod assay and the fact that it takes 20 minutes to complete intra-nasal drug delivery, this experiment is performed twice (6 animals per chronic protocol; n=3 rats sacrificed immediately post the sleep deprivation period and n=3 rats sacrificed after RS). The EEG/EMG data is analyzed as detailed above. For the roto-rod testing, the amount of time each rat spends on the wheel is analyzed and compared to control. Qualitative and quantitative analysis sets are generated and descriptive statistical comparisons and two-way ANOVA with post hoc multiple comparisons are used to evaluate changes in behavior/wheel running as a function of the day and drug, assuming equal variances. Our results confirm the effectiveness of intranasal delivery of modafinil under chronic stressful conditions.

4. Efficacy of our intranasal drug delivery in chronically sleep deprived humans is also readily confirmed using established methods. Our preferred protocol is based on the results of a series of experiments that tested the treatment efficacy of a hypnotic-stimulant combination to maintain sleep quality, performance, and alertness (Batéjat, et al., Aviat Space Environ Med. 2006 May; 77(5):515-25). Here, healthy male subjects are given zolpidem then allowed to sleep for 6 h prior to being subjected to a simulated military operation of 18 h continuous work. Modafinil (2, 10, 50 and 200 ug dosage treatment groups) is administered using (a) VIANASE electronic atomizer (Bothell, Wash.) or (b) OPTINOSE nasal delivery system (Oslo, Norway) 9 h into the work period. The effects of drugs on sleep-wake behavior (EEG recordings), cortical activation (Critical Flicker Frequency test) and performance levels (reaction time, memory search, attention, dual task, computerized Stroop tests) are monitored. All modafinil test groups maintain elevated performance and alertness over LME-only negative controls and even over systemically-administered modafinil positive-controls throughout the 18 h work period.

Preparation of Modafinil-Lme (Store all Modafinil Solutions in the Dark and at Room temperature).

(a) Preparation of Lipid Micro Emulsion (LME)

1. 84.4 mg phosphotidylserine (Avanti Polar Lipids), 91.72 uL olive oil (Sigma Aldrich), and 3.82 mL 50 mM sodium Succinate buffer (Sigma Aldrich, pH 4.25) were combined in a 15 mL conical tube and vortexed.

2. An ice bath was prepared containing ~10 g sodium chloride to lower the temperature near −10° C.

3. The conical tube was lowered into the ice bath and fitted with a probe sonicator. The sonicator tip was placed just above the bottom of the tube and checked to make sure the tip was not touching the sides of the tube.

4. The probe sonicator was placed on setting 10 with a 25% on/off cycle and a period of 20 seconds for an average power output of 22 watts.

5. The ice bath was replaced every 30 min to maintain a constant temperature.

6. After 4 h, the sonicator was turned off and the solution was evenly distributed to 3 1.5 mL microcentrifuge tubes. The solution was transparent and appeared amber in color only when held up to light.

7. The tubes were centrifuged for 11 min at 8,000 RPM to remove metal particulates from the probe tip.

8. The LME was then transferred to 4 clean microcentrifuge tubes, each containing approximately ~1 mL LME.

9. The LME was then passed through a 0.2 micron filter (from MILLIPORE) after centrifugation.

Preparation of 0.2 mg/mL Modafinil-LME 1. 5 mL LME (made using the above procedure) was titrated to pH 8 using 5 N NaOH.

2. 1 mg modafinil (Sigma Aldrich) was added to a clean 10 cm glass culture tube.

3. The LME (5 mL) was added to the glass culture tube containing the modafinil. The tube was covered lightly with parafilm and briefly vortexed.

4. The mixture was then placed in the bath sonicator, covered with a cardboard box to protect from light, and sonicated at room temperature for several hours.

5. The water temperature was checked every ½ h to ensure a temperature at or below 37° C.

6. After several hours, the solution was again transparent and amber when held up to light. There were no visible particles of modafinil in the solution.

7. 1 mL aliquots were then made in 1 mL microcentrifuge tubes and placed in a dark cabinet to evaluate stability over several weeks.

8. For the next two weeks, the solution was checked daily for particulate matter. The solution remained transparent, free of precipitates, and amber only when held up to light.

Preparation of Modafinil-LME at Physiological pH 1. 1 mL modafinil-LME (0.5 mg/mL) was transferred to a clean 1.5 microcentrifuge tube.

2. The pH of the modafinil-LME was adjusted from 8.0 to 7.0 using 1 M HCl and pH test strips (SIGMA ALDRICH). The appearance of the modafinil-LME solution turned slightly cloudy upon the addition of the 1 M HCl.

3. The pH of another 1 mL modafinil-LME sample (0.5 mg/mL) was adjusted to 7.4 using 1 M HCl and pH test strips, as above.

4. Both pH adjusted samples were returned to storage in a dark cabinet at room temperature for later analysis.

5. In an alternative embodiment, (i) the modafinil is pre-dissolved in a physiologically-acceptable cosolvent such as ethanol or final concentration-minimized DMSO; and/or (ii) the initial sonication is at pH 8.

The descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for delivering modafinil selectively to the brain, minimizing delivery to the blood, of a person in need thereof, comprising: administering to the person a therapeutically-effective dosage of modafinil, wherein the dosage is from 2 to 200 ug, formulated in a lipid microemulsion (LME) and selectively delivered to the upper third of the nasal cavity, sufficient to increase wakefulness or reduce sleep or sleepiness.

2. The method of claim 1, wherein the dosage is from 2 to 100 ug.

3. The method of claim 1, wherein the dosage is from 10 to 50 ug.

4. The method of claim 1, wherein the dosage is formulated in the LME by adding the modafinil to the LME at pH 7-9.

5. The method of claim 1, wherein the dosage is formulated in the LME by adding the modafinil dissolved in DMSO to the LME, wherein the final DMSO concentration is less than 1%.

6. The method of claim 1, wherein the dosage is formulated in the LME at a concentration of 0.02 to 2 mg/ml.

7. The method of claim 1, wherein the dosage is formulated in the LME at a concentration of 0.02 to 0.2 mg/ml.

8. The method of claim 1, wherein the dosage is administered in a volume of 10 to 400 ul.

9. The method of claim 1, wherein the dosage is administered in a volume of 100 to 250 ul.

10. The method of claim 1, wherein the LME is made of equal amounts of olive oil and phosphatidylserine sonicated in succinate buffer at pH 4.25, then titrated to pH 8.

11. The method of claim 1, wherein the modafinil is the R-enantiomer (Armodafinil).

12. The method of claim 1, whereby at least 0.02% of the dosage is delivered to the brain within 20 minutes post-administration.

13. The method of claim 1, whereby less than 50% of the dosage is delivered to the blood 20 minutes post-administration.

14. The method of claim 1, wherein the method further comprises the antecedent step of formulating the modafinil in the LME.

15. The method of claim 1, wherein the method further comprises the antecedent step of formulating the modafinil in the LME, and between the formulating and administering steps the modafinil is protected from light and maintained at room temperature.

16. The method of claim 1, wherein the method further comprises the subsequent step of detecting a resultant therapeutic effect.

17. The method of claim 1, wherein the method further comprises the subsequent step of detecting a resultant therapeutic effect that is an increase in wakefulness or reduction in sleep or sleepiness.

18. The method of claim 1, wherein the method further comprises the subsequent step of detecting or quantifying a resultant delivery of the modafinil to the brain or blood.

19. The method of claim 1, wherein the dosage is selectively delivered to the upper third of the nasal cavity using a VIANASE electronic atomizer or an OPTINOSE nasal delivery system.

20. A method for delivering modafinil selectively to the brain, minimizing delivery to the blood, of a person in need thereof, comprising: administering to the person a pharmaceutical composition consisting essentially of a therapeutically-effective, unit dosage of modafinil, wherein the dosage is from 2 to 200 ug, formulated in a lipid microemulsion (LME) and selectively delivered to the upper third of the nasal cavity, sufficient to increase wakefulness or reduce sleep or sleepiness.

21. The method of claim 20 wherein the administering step is effected with an intranasal pharmaceutical delivery device loaded with the composition, and adapted to deliver the dosage to the upper third of the nasal cavity.

* * * * *